United States Patent
Yoshinari et al.

(10) Patent No.: US 8,043,685 B2
(45) Date of Patent: Oct. 25, 2011

(54) SHEET HAVING ELASTIC PROPERTY AND SLIP PROPERTY, AND SOLVENT DISPENSING CONTAINER USING THE SHEET

(75) Inventors: Kiyoshi Yoshinari, Kamakura (JP); Hideo Shimura, Tokyo (JP); Kazumasa Kinoshita, Fujisawa (JP)

(73) Assignee: Chugai Seikaku Kabushikikaisha, Tokyo (JP)

( * ) Notice: Subject to any disclaimer, the term of this patent is extended or adjusted under 35 U.S.C. 154(b) by 751 days.

(21) Appl. No.: 10/593,747

(22) PCT Filed: Mar. 28, 2005

(86) PCT No.: PCT/JP2005/005684
§ 371 (c)(1), (2), (4) Date: Dec. 14, 2007

(87) PCT Pub. No.: WO2005/092734
PCT Pub. Date: Oct. 6, 2005

(65) Prior Publication Data
US 2008/0210691 A1      Sep. 4, 2008

(30) Foreign Application Priority Data
Mar. 26, 2004  (JP) .................. 2004-091741

(51) Int. Cl.
*B32B 3/10* (2006.01)
(52) U.S. Cl. ........ 428/131; 428/421; 428/422; 428/500; 428/35.7; 428/36.9; 428/36.8
(58) Field of Classification Search .................. 428/421, 428/422, 34.1, 35.7, 36.9, 36.91, 131, 500, 428/36.8; 422/102, 103, 104, 58, 99
See application file for complete search history.

(56) References Cited

U.S. PATENT DOCUMENTS

| | | | |
|---|---|---|---|
| 4,362,698 A | * | 12/1982 | Boosalis et al. ............. 422/102 |
| 2004/0096622 A1 | * | 5/2004 | Razavi et al. .................. 428/98 |

FOREIGN PATENT DOCUMENTS

| JP | 58-32345 | 8/1981 |
|---|---|---|
| JP | 58-46777 | 3/1983 |
| JP | 5-154962 | 6/1993 |
| JP | 08-301322 | 11/1996 |
| JP | 10-132713 | 5/1998 |
| JP | 11-241718 | 9/1999 |
| JP | 2003-236989 | 8/2003 |

* cited by examiner

*Primary Examiner* — Michael C Miggins
(74) *Attorney, Agent, or Firm* — Michaelson & Associates; Peter L. Michaelson

(57) ABSTRACT

The object of the present invention is to provide a sheet applicable for closing an opening of a liquid dispensing container for a liquid handling system used in chemical experiments, in which the sheet is capable of preventing natural volatilization of a liquid in the container even if the tip is frequently inserted and drawn, and also facilitating inserting and drawing of the tip. The composite sheet of the present invention comprises a sheet having elastic property and another sheet having slip property wherein the sheets are stacked.

The composite sheet of the present invention can be used to close an opening of a liquid dispensing container for a liquid handling system used in chemical experiments. It can prevent volatilization of the solvent, and also facilitate inserting and drawing of the tip.

8 Claims, 16 Drawing Sheets

(a)

(b)

(c)

(a)

(b)

(a)

(b)

(a)

(b)

SHEET HAVING ELASTIC PROPERTY AND SLIP PROPERTY, AND SOLVENT DISPENSING CONTAINER USING THE SHEET

TECHNICAL FIELD

The present invention relates to a sheet used in a liquid dispensing container for a liquid handling system used in chemical experiments and the like and a container using the sheet.

BACKGROUND ART

In a liquid handling system used in chemical experiments and the like, liquid is transferred (dispensed) into and out of a liquid dispensing container (hereinafter, referred to as a "tank" in the description) using a tip for a pipet (hereinafter, simply referred to as a "tip" in the description) for subsequent tests.

When dispensing a relatively low volatile liquid (water, various salt solutions and the like) to a tank, an open-topped tank 50, shown in FIG. 14, has been used because the liquid will not lose in weight even if the tank is open.

On the contrary, when dispensing a relatively high volatile liquid (organic solvent, such as ethanol, methanol and acetonitrile) to a tank, the opening of the tank 50 is usually closed with a lid 52 because the liquid may lose in weight owing to its high volatile characteristics. And, when the liquid is dispensed into and out of the tank 50 using a tip 51, the lid 52 is detached from the tank 50.

However, in a case in which the tank 50, shown in FIG. 14, is used, the tank 50 cannot be tightly sealed even if this kind of lid 52 is used, and thus loss in weight of organic solvent owing to volatilization cannot be prevented. If the organic solvent in the tank 50 loses in weight, the initially transferred solvent may be reduced in amount. In a result, a problem of inaccuracy of quantitative analysis may be caused. Today, because of progress in microanalytical technique, volatilization of organic solvent will significantly affect a result of analysis. In addition, requiring to attach and detach the lid 52 every dispensing works leads to a problem in lowering operating efficiency of the dispensing operation and the subsequent tests.

Furthermore, as a tip 51 for a pipet, one made of resin having a higher chemical resistance than one made of metal has been in use. So, in view of sealing property of the tank, a septum, what is called, is proposed. However, the septum is only used for inserting a metal tip (needle) and therefore cannot resist several time of inserting and drawing of the tip. So, the septum is not applicable for practical use.

Consequently, to employ a tip made of resin, as shown in FIG. 15, a tank 50, the opening of which is covered with a sheet 53 having a single straight slit 54, is proposed. However, frequent inserting and drawing of the tip 51 and/or employing a plurality of tips 51 may cause significantly wear of the sheet 53 around the slit 54. As a result, the slit 54 remains opened and thus cannot be tightly closed. So, volatilization of the liquid and thus loss in weight of the liquid cannot be prevented.

To solve the problems, a tank 50 the opening of which is covered with a sheet 53 having a plurality of radial slit 55, as shown in FIG. 16, is proposed.

The radial slits 55 are formed corresponding to the tips 51. For example, when a series of eight tips 51 are used, the sheet 53 has eight of the radial slits 55.

However, when frequent inserting and drawing of the tip 51 increase, a friction between the slit 55 and the chip 51 deforms the radial pieces 55a and 55b of each slit 55. Consequently, sealing performance of the tank 50 still remains low.

DISCLOSURE OF THE INVENTION

Figure 1:
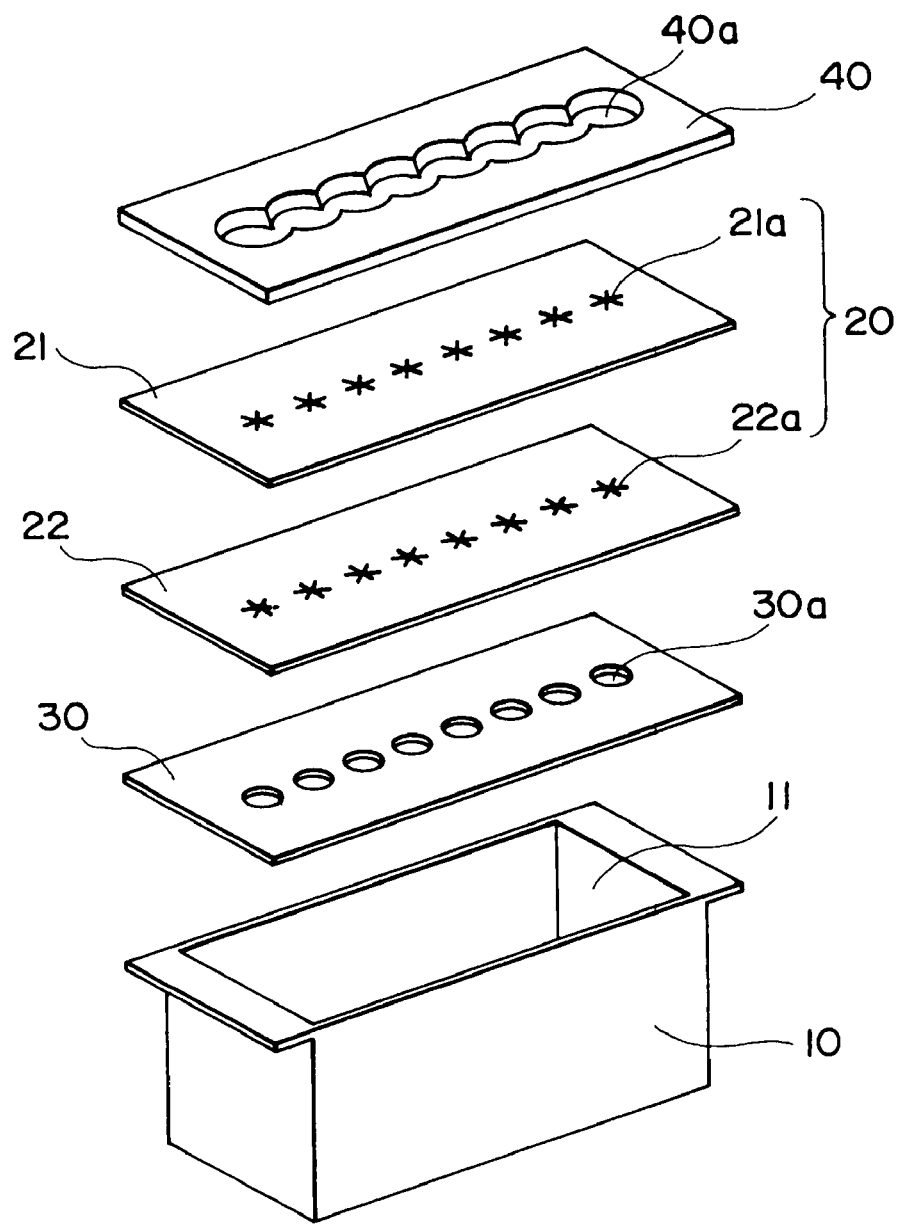
FIG. 1 Exploded perspective drawings showing a state in which a liquid dispensing container.

Problems to be Resolved by the Invention

Accordingly, the object of the present invention is to provide a sheet applicable for closing an opening of a liquid dispensing container for a liquid handling system used in chemical experiments, in which the sheet is capable of preventing natural volatilization of a liquid in the container even if the tip is frequently inserted and drawn, and also facilitating inserting and drawing of the tip.

Means of Solving The Problems

The inventors of the present invention carried out an in-depth study to accomplish the object. As a result, he has found this object can be accomplished by using a sheet produced by stacking specific sheets.

The present invention has been accomplished based on the above finding and provide a composite sheet comprising a sheet having elastic property and another sheet having slip property wherein the sheets are stacked.

And, the present invention provides a container for dispensing liquid contained therein through an opening which is covered with a composite sheet comprising a sheet having elastic property and another sheet having slip property wherein the sheets are stacked.

Effect of the Invention

According to the present invention, the slip property of the sheet allows the tip to be inserted and drawn with small resistance. And, the elastic property of another sheet shows restoring force to restore the sheet. Accordingly, the container is maintained sealed regardless of the number of inserting and drawing of the chip. In addition, when the tip of the pipet is drawn out of the container after sucking liquid from the container, the tip is wiped with the slit pieces of the sheet, whereby excess liquid attached to the outer surface of the tip, such as droplets attached to the tip, can be removed. So, a predetermined amount of the liquid can be correctly measured.

PREFERRED EMBODIMENT OF THE INVENTION

Hereinafter, preferred embodiments of a composite sheet of the present invention will be described.

A composite sheet according to the present invention comprises a sheet having elastic property and another sheet having slip property wherein the sheets are stacked.

A composite sheet of the invention is employed for closing an opening of a liquid dispensing container for a liquid handling system used in chemical experiments. Specifically, the composite sheet is employed for closing an opening through which liquid is dispensed in and out of a liquid dispensing container. That is, the composite sheet of the present invention can be employed as a sheet for closing an opening of a liquid dispensing container.

Hereinafter, a case in which a composite sheet of the present invention is employed for closing an opening of the aforesaid container will be described referring to the drawings.

Figure 2:
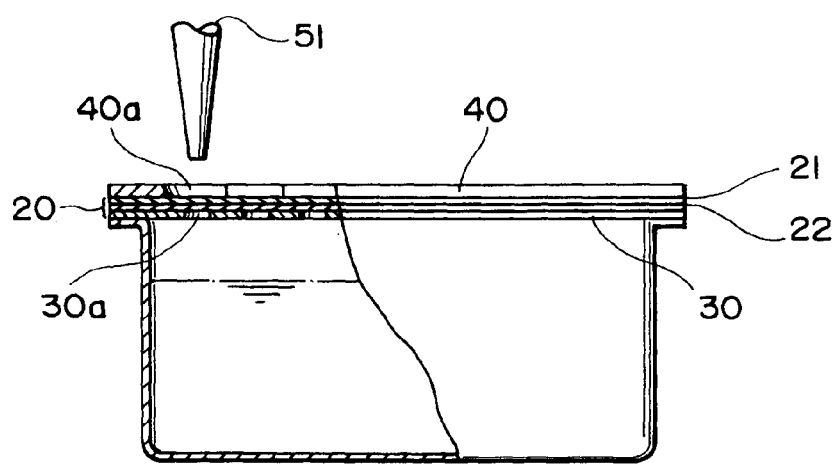
FIG. 2 A partial cross-section drawings showing an operation for transferring (dispensing) liquid.

FIG. 1 is an exploded perspective drawing showing a state in which a liquid dispensing container (hereinafter, referring to as a "tank" in the description) 10 is covered with a sheet 20. FIG. 2 is a partial cross-section drawing showing an operation for transferring (dispensing) liquid 12 by using a tip 51 in and out of the tank 10 the opening of which is covered with the sheet 20.

As shown in the figures, the tank 10 is equipped with the sheet 20 which covers the opening 11 of the tank 10.

Usually, the opening 11 is equipped with a base plate 30 for supporting the sheet 20, and the sheet 20 is placed on the base plate 30.

And, on the sheet 20, a clamp plate 40 is placed.

The tank 10 may be made of any materials used in a container for a liquid handling system used in chemical experiments without limitation, preferably, made of materials having resistance to organic solvents because the tank is sometimes used for containing chemical solvent. As such materials, polyethylene, polypropylene and polycarbonate may be given.

The base plate 30 may be made of any materials used in a base plate for a liquid handling system used in chemical experiments without limitation. As such materials, polyethylene, polypropylene, polycarbonate, polytetrafluoroethylene, stainless steel, aluminum and polyimide may be given.

The clamp plate 40, made of metal plate, clamps the sheet 20 between the base plate 30 and itself due to its own weight for restricting deflection and displacement of the sheet 20.

The base plate 30 is formed with pluralities of bores 30a, and the clamp plate 40 is formed with pluralities of bores 40a. The bores 30a and the bores 40a are arranged in the same positions as slits, described below, in the vertical direction.

The composite sheet 20 comprises a "A" sheet 21 and a "B" sheet 22 wherein the sheets are stacked.

The "A" sheet 21 is made of sheet materials having small resistance for inserting and drawing the tip 51, that is, sheet materials having slip property. Specific preferable examples of sheet materials having slip property may be ones having both coefficient of dynamic friction and coefficient of static friction, the both of the coefficients being 0.2 or lower, depending on materials and shapes of the tip and shapes of the slit. The coefficient of dynamic friction and the coefficient of static friction are measured in accordance with ASTM-01894-63.

As the sheet materials having slip property, polypropylene (PP) and polyethylene (PE), polymethylpentene(PMP), each having a thickness of 0.5 mm or smaller, and polytetrafluoroethylene (PTFE) having a thickness of 1 mm or smaller will be specifically given. Especially, PTFE is an ideal sheet material because of its small coefficient of friction of 0.1 to 0.05 or smaller.

The "B" sheet 22 is made of sheet materials having elastic force for restoring the slit pieces (shown in FIG. 3) even if inserting and drawing of the tip 51 are carried out frequently, such as sheet materials having elastic property.

As the sheet materials having elastic property, sheet materials having hardness Hs of 30° to 90° and coefficient of restitution of 20% to 50% are preferably selected depending on materials and shapes of the tip and thickness of the sheet. Specifically, silicon rubber having a thickness of 0.5 to 1.0 mm is preferably employed. The hardness is measured in accordance with JIS K 6253 and the coefficient of restitution is measured in accordance with JIS K 6253.

In exchange of silicon rubber, fluorocarbon rubber, perfluoro (perfluoro elastomer) rubber, nitrile rubber, chloroprene rubber, ethylene-propylene rubber and polyimide resin may be given. The kind of the sheet material is selected depending on heat resistance, chemical resistance and oil resistance according to liquid contained in the tank. If employed under an area requiring light shielding (RI and the like), the sheet made of sheet materials which hardly transmits light, such as black silicone rubber and black fluorocarbon rubber, may be selected for light shielding.

In order to improve sealing performance, a supporting tool having no slit and hole may be placed on the "B" sheet. The supporting tool may be made of polyimide and aluminum.

The A sheet 21 and the B sheet 22 may be arranged such that the both sheets are simply stacked or bonded with adhesive. When the both sheets are bonded together, at least one sheet may be coated by a coating method.

Each of the A sheet 21 and the B sheet 22 is preferably formed with a slit (a cut). And, the slit may be shaped into a radial shape (shown in FIGS. 3(a) and (b)), a cross shape (shown in FIG. 4(a)) or a straight line shape (shown in FIG. 4(b)) The sheets are preferably arranged such that the slits formed at respective sheets are conformed each other in the vertical direction. Preferably, the slits formed at the sheet having elastic property is substantially conformed with the slits formed at the sheet having slip property.

Figure 5:
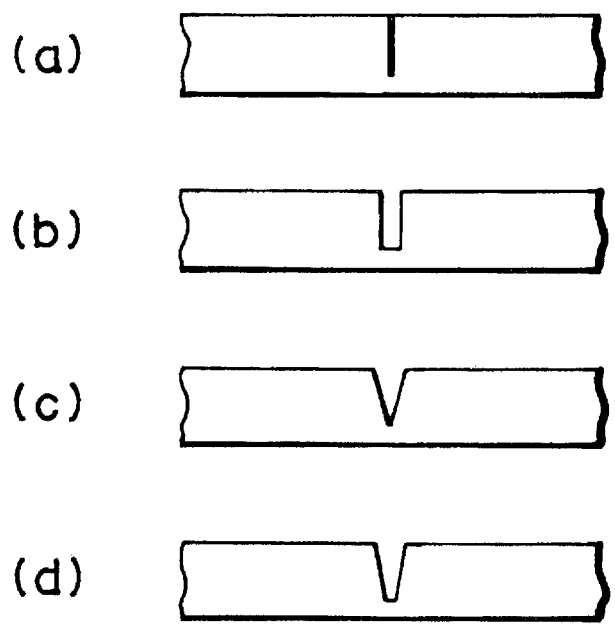
FIG. 5 Cross-section drawings showing the shapes of the sheets of this invention.

The slit may be formed to cut the sheet completely or incompletely. That is, the slit does not need to penetrate through the sheet in the thickness direction or may terminate at the middle of the sheet in the thickness direction. FIG. 5 are cross-section drawings showing the shapes of the slits formed in the sheet. FIG. 5(a) shows a slit having little width; FIG. 5(b) shows a slit having a certain width; FIGS. (c) and (d) show V-shaped slits. As shown in figures, the slit may have various shapes.

By using the sheet having the aforesaid shaped slits, the container will be maintained sealed while a reaction continues and thus a procedure for transferring liquid out of the tank using a tip is not carried out, because the slit is not penetrated through the sheet. In addition, the tip can be easily inserted to the container through the slit when the liquid after the reaction is transferred out of the tank using the tip. That is, since the slits terminate at the middle in the thickness direction of the sheet, the tip tears the sheet easily at the slit so as to penetrate through the sheet.

In addition, when the tip of the pipet is drawn out of the tank after suction of liquid, the outer surface of the tip is wiped with the slit pieces of the sheet. Therefore, excess liquid attached to the surface of the tip, such as droplets attached to the surface of the tip, is removed. Accordingly, a predetermined amount of liquid can be measured correctly.

As a suitable example employing the container, a laboratory device necessary for genetic manipulation in molecular biology field, that is PCR (polymerase chain reaction), will be given The PCR is a method for amplifying a small amount of target specific DNA sequences using heat-resistant DNA polymerase in a container.

Conventionally, in such a type of PCR, liquid is repeatedly reacted for about 25 times at a temperature cycling, for example, from 55° C. to 94° C. By the reaction, the inside of the container becomes a high pressure and high temperature state. In order to prevent volatilization of the liquid, the container is tightly sealed with a lid until the reaction finishes.

So, it is not easy to transfer the liquid out of the container because the container is tightly sealed with the lid. When the liquid is transferred out of the container, the lid which tightly seals the container has to be removed. This procedure complicates the experiment work.

In order to resolve the complication, the container may be sealed with "the aforesaid sheet having the slits penetrating the sheet incompletely". By using this sheet, the container can be maintained at the sealed condition during the reaction, and the tip can be easily inserted through the slit when the solvent is transferred out of the container.

Next, a dispensing work using the sheet 20 formed with the radial slits will be described referring to FIG. 2 and FIG. 3.

The dispensing work is explained as for one tip 51. Firstly, the distal end of the tip 51 is inserted into the radial slit 21a formed at the A sheet 21 through the opening 40a of the clamp plate 40. As shown in FIG. 3(a), the tip 51 is freely inserted because each of slit pieces 21b, 21c is made of materials having large slip property.

Then, in the same way, the distal end of the tip 51 is inserted into the slit 22a of the B sheet 22, shown in FIG. 3(b), and after a predetermined amount of liquid 12 is poured to the tank 10 by the tip 51, the tip 51 is drawn out.

When the tip is drawn out, each of slit pieces 21b, 21c of the slit 22a is resiliently restored because of large elastic property of the B sheet 22. As a result, the slit is closed with the slit pieces 21b and 21c for maintaining the container 10 at the sealed condition. Besides, the A sheet 21 is not worn by friction with the tip 51 because of its slip property.

As mentioned above, easy inserting and drawing of the tip and sealing performance of the tank can be maintained even though inserting and drawing of the tip 51 are frequently conducted.

The aforementioned result can be applied to a case in which a number of the tip 51 is not only one but also plural (8 in the example shown in FIGS. 24, 96, 384, 1536 and the like). So, the radial slits 21a, 22a corresponding to any tips will allow easy inserting and drawing of the tip 51 and tight sealing of the container thereby preventing natural volatilization of liquid contained in the tank 10.

The radial slits 21a and 22a formed at the A sheet 21 and the B sheet 22 respectively are shaped to radiate out from centers 21o and 22o. In this case, depending on a thickness of the sheet, a slit may be extended and, for example, may be communicated with adjacent slits and may end up spreading over the sheet. This leads to lowering operationality. To avoid this, ends of the slit are terminated with bores or lines, if necessary. FIGS. 3(a) and (b) show radial slits, each end of which terminates with a bore; FIG. 3(c) shows a radial slit each end which terminates with a line.

The slits 21a and 22a are arranged in such a manner that the centers 21o and 22o are located at the same position in the vertical direction, and that the cut lines of the slits are substantially conformed each other on plane so as to achieve smooth inserting and drawing of the tip 51. On the contrary, as shown in FIGS. 3(a) and (b), in order to maintain the sealing performance, the cut lines of the slit 21a may not be conformed with the cut lines of the slit 22a. That is, each cut line of the slits shown in FIGS. 3(a) and (b) is displaced at about 45°. Displacing the cut lines of the slits each other means displacing the slit 21a relative to the slit 22a at about 22.5°. Displacing the slit 21a relative to the slit 22a at about 22.5° allows further improvement of the sealing ability of the tank.

Figure 3:
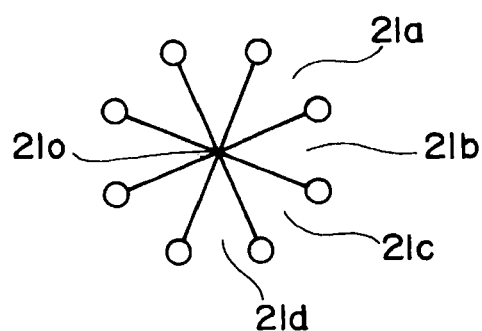
FIG. 3 A drawing showing radial slits.
Figure 3:
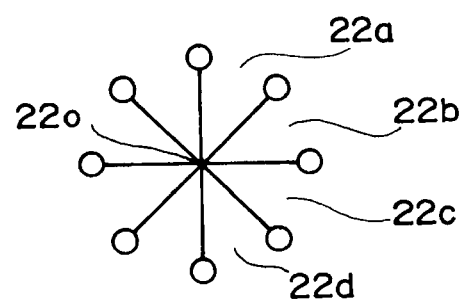
Figure 3:
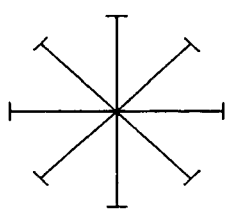
Figure 4:
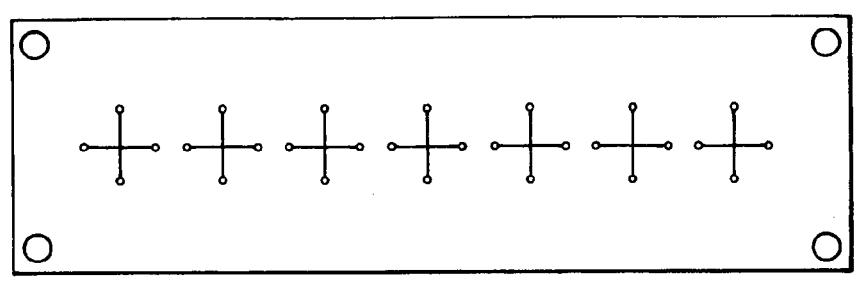
FIG. 4 A drawing showing another embodiment of slits.
Figure 4:
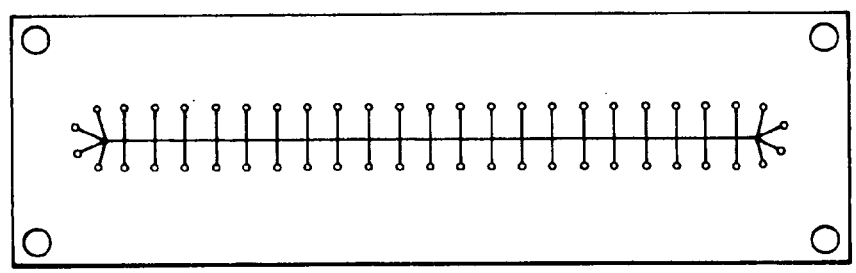
Figure 6:
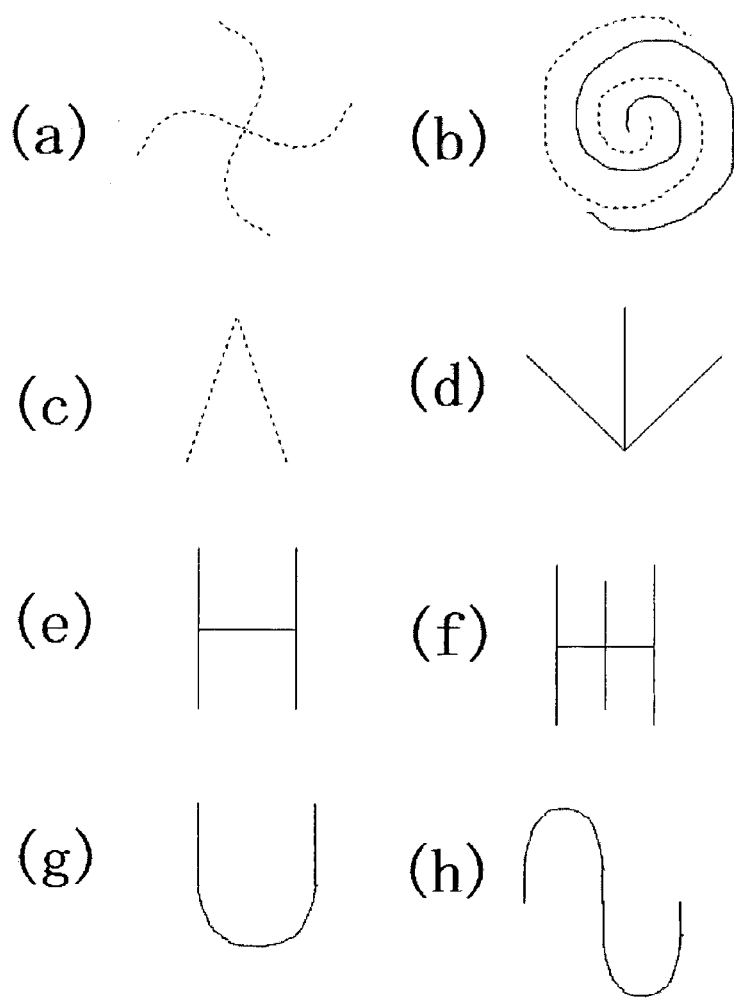
FIG. 6 A drawing showing another embodiment of slits.

The slit may have any shapes, without limitation, capable of smoothly inserting and drawing the tip, for example, shapes shown in FIG. 6, in addition to the radial shapes shown in FIG. 3. FIG. 6(a) shows a swastika-shaped slit; FIG. 6(b) shows a turbinated-shaped slit; FIG. 6(c) shows a V-shaped slit; FIG. 6(d) shows an arrow-shaped slit; FIG. 6(e) shows a H-shaped slit; FIG. 6(f) shows the slit shown in FIG. 6(e) added with one cut line; FIG. 6(g) shows a U-shaped slit; and FIG. 6(h) shows a S-shaped slit. In a sheet according to the present invention, the slit may have any shapes for permitting smooth inserting and drawing of the tip, not limited to the aforesaid ones.

A composite sheet according to the present invention comprises a sheet having elastic property and another sheet having slip property wherein the sheets are stacked. In the present invention, the sheets may or may not have the same shape. When the sheets have the same shape, the cut lines of the slits may or may not be conformed to each other.

Heretofore, a case of the liquid dispensing container (tank) 10 having one opening 11, that is, the container having one storage space for liquid, has been described; however, the liquid dispensing container according to the present invention is not limited to.

Accordingly, the present invention can be applicable to the tank 10, shown in FIG. 7(a), the inside of which is divided into storage spaces each having an opening 11. Such types of the tank are employed in a liquid handling system which dispenses different liquids so as to achieve efficient and speedy dispensing work.

The sheet 20 which covers the tank 10 is formed with the slits (21a and 22s), same as the above-mentioned, correspondent to the openings 11 shown in FIG. 7(a). And, on the dispensing work, the tip is inserted in each slit, and after pouring liquid into the storage space, the tip is drawn out.

Figure 7:
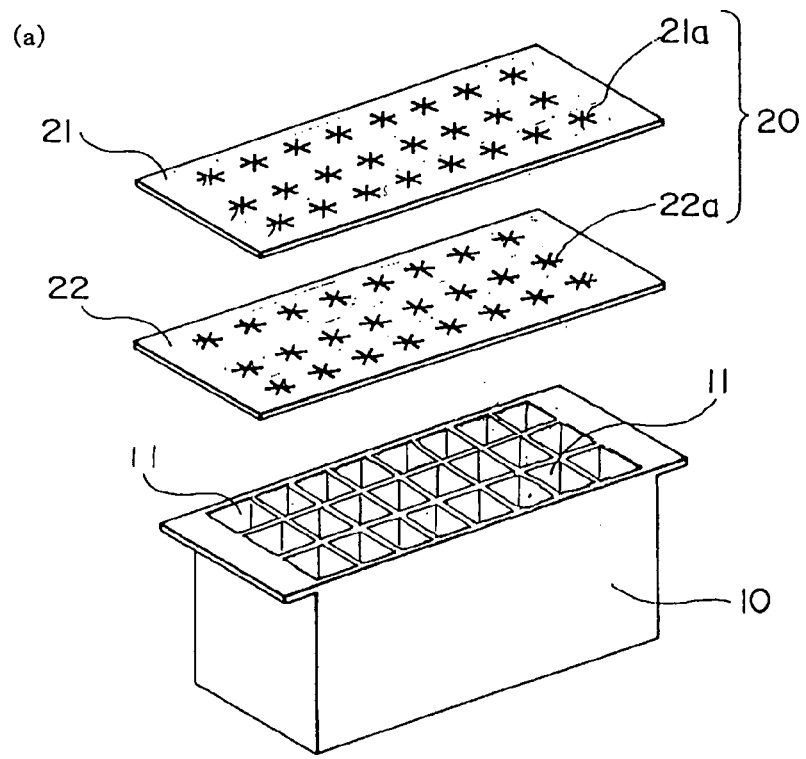
FIG. 7 A drawing showing another embodiment of a liquid dispensing container.
Figure 7:
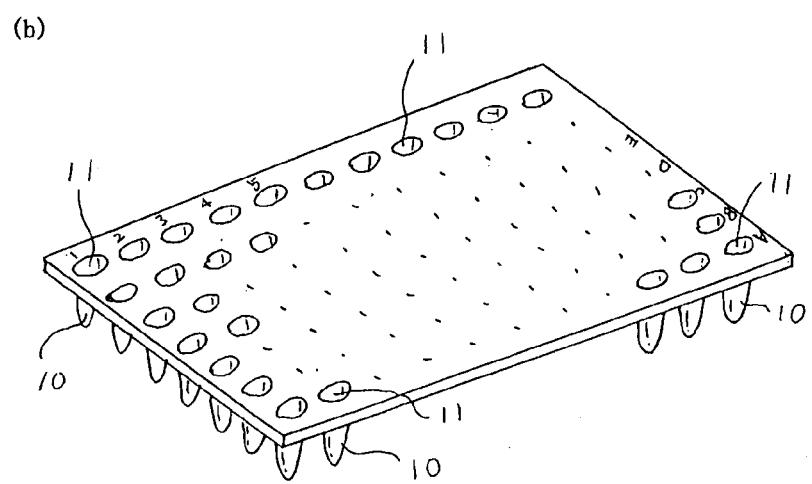

A liquid dispensing container shown in FIG. 7(b) is equipped with pluralities of tubular tanks 10. In this container, each tank 10 has individual opening 11 and individual storage space. The tubular tanks 10 are arranged (integrated) lengthwise and crosswise depending on one's need (as shown in FIG. 7). The liquid dispensing container, shown in FIG. 7(b), has the tubular tanks arranged in 8 rows crosswise and 12 rows lengthwise, in a total number of 96.

The container is covered with the sheet, not shown, such that the slits of the sheet are positioned above the tubular tanks 10 respectively, as the same way mentioned-above. The tubular tank 10 may be one at minimum. Alternatively, when plural dispensing works are carried out, the tubular tank 10 may be formed in plural equal to the number of the dispensing works. In any cases, the container significantly contributes on high efficiency and speeding up of the dispensing work.

As mentioned above, the clamp plate 40, made of metal plate, clamps the sheet 20 between the base plate 30 and itself due to its own weight for restricting deflection and displacement of the sheet 20. When pluralities of tips 51 (96 in the example shown in FIG. 7(*b*), for example, 8, 16, 24, 48, 384, 1536) are used for simultaneous dispensing works, the base plate 30, the sheet 20 and the clamp plate 40 may be floated because of friction between the sheet 20 and the tips 51. Consequently, an embodiment of the clamp plate capable of solving the problem will be described referring to drawings.

Figure 8:
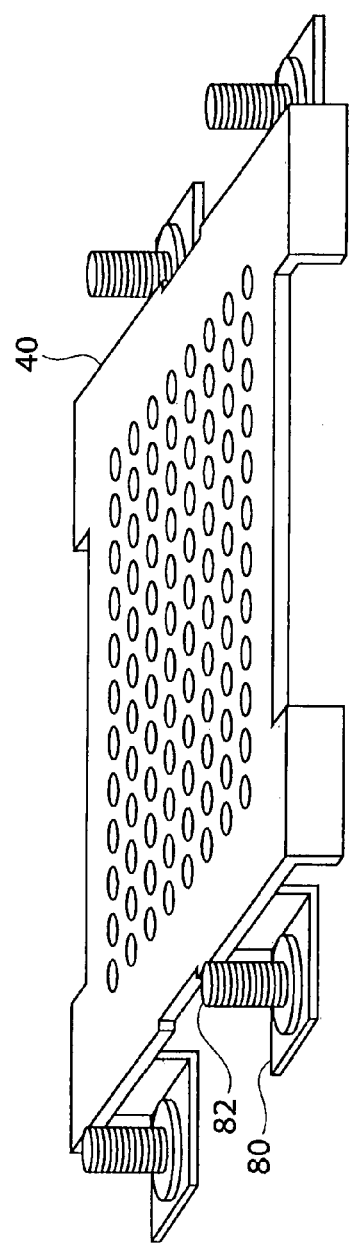
FIG. 8 A drawing showing the base plate with an elastic member for preventing the base plate floating.

FIG. 8 is a drawing showing another embodiment of the clamp plate. The clamp plate 40 is provided with supporting plates 80 on which an elastic member 82, such as a spring, is mounted at side surface thereof so as to prevent the base plate 30, the sheet 20 and the clamp plate 40 from floating at dispensing work. The tank 10 is movable by means of a liquid handling system in order to be adapted to a case in which an experiment is carried out with temperatures being varied depending on reaction. When the liquid handling system moves the tank, the liquid handling system contacts the tank and then the elastic member 82 mounted to the clamp plate 40 contacts a member (not shown) of the liquid handling system. Then, when the tip may be drawn, the elastic member 82 functions to push back the member. As the result, the liquid handling system is easily separated from the clamp plate 40, whereby the clamp plate 40, the base plate 30 and the sheet 20 are prevented from floating. In addition, because of the increased weight of the tank 10 by the weight of the elastic members added thereto, close contact between the sheet 20 and the tank 10 can be strengthened and therefore sealing performance of the tank can be improved.

Figure 9:
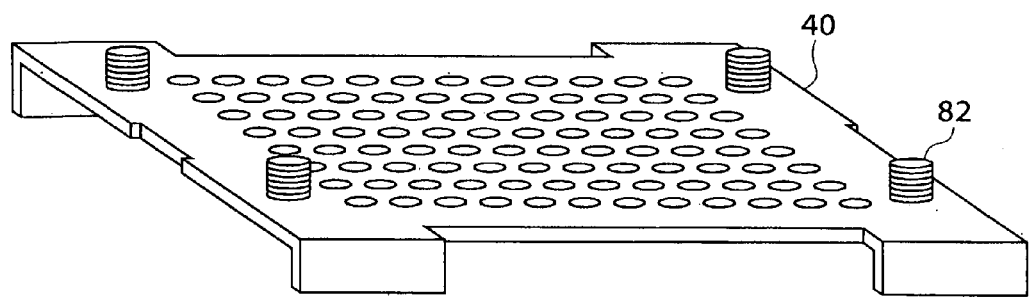
FIG. 9 A drawing showing the base plate with an elastic member for preventing the base plate floating.

FIG. 9 is a drawing showing still another embodiment of the clamp plate. In the clamp plate 40 shown in FIG. 9, the elastic members are mounted the clamp plate 40 directly. The clamp plate of the embodiment shows promise for the same effect and operation as that of FIG. 8.

Figure 10:
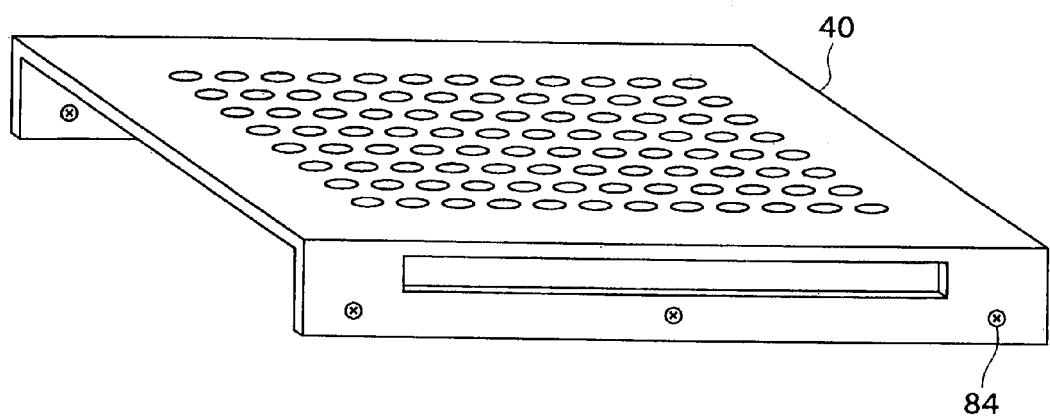
FIG. 10 A drawing showing the base plate with screws for preventing the base plate floating.

FIG. 10 is a drawing showing still another embodiment of the clamp plate. The clamp plate 40 of the embodiment is fixedly mounted to the tank with fixing members such as screws 84. Accordingly, the clamp plate 40, base plate 30 and the sheet 20 are prevented from floating.

Figure 11:
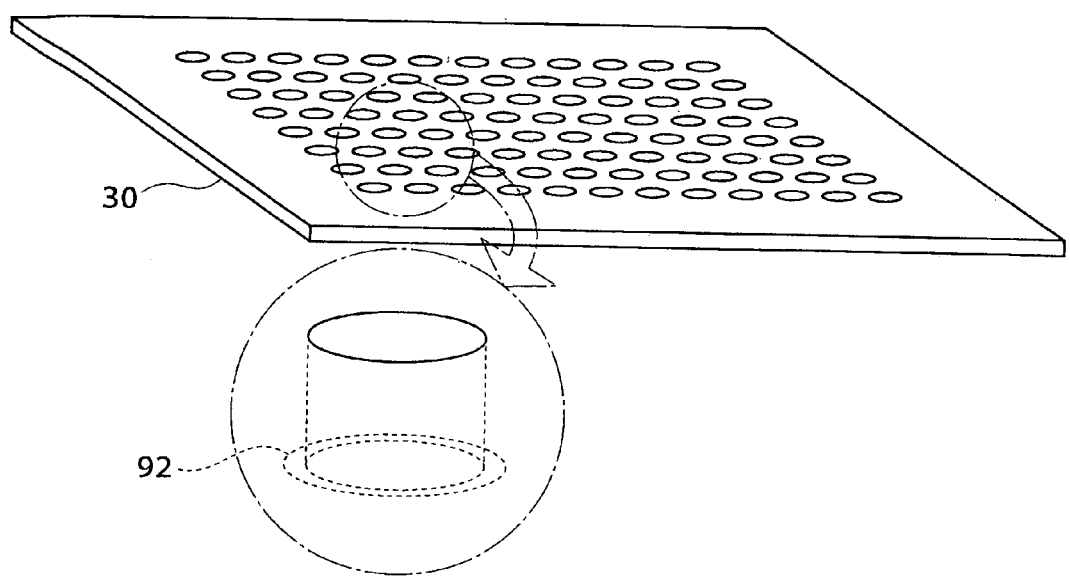
FIG. 11 A drawing showing the base plate with grooves 92 at portions which contact.
Figure 11:
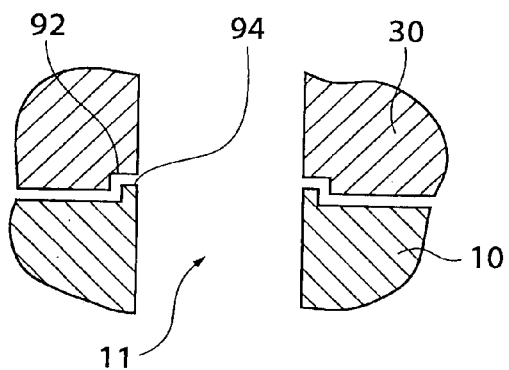

In the liquid dispensing container equipped with pluralities of tubular tanks 10 shown in FIG. 7(*b*), as the number of the tubular tanks increase, sealing ability between the sheet 20 and rims of the openings 11 of the tank 10 may deteriorate, thereby causing volatilization of the solvent in the tank. The rim of the opening 11 of each tubular tank may rise from an area around the rims; that is, the opening may be bordered with a projected portion. So, if the base plate 30, the sheet 20 and the clamp plate 40 are placed on the projected portions, a space is formed between the base plate 30 and the openings 11 of the tubular tanks, through which solvent in the tank may volatize. FIG. 11(*a*) is a perspective drawing showing another embodiment of the base plate 30, and FIG. 11(*b*) is an enlarged cross-section drawing showing the base plate 30 which is placed on the tank 10. Partially enlarged perspective drawing is shown in a circle in the figure. As shown in FIG. 11, the base plate 30 is formed with grooves 92 at portions which contact the liquid dispensing container. In the grooves 92, the projected portions around the openings 11 of the container are engaged so that the space may not be formed. Therefore, the solvent in the tank is prevented from volatilization. When the opening 11 is bordered with a projected portion 94 as shown in FIG. 11(*b*), the base plate 30 is preferably formed with the groove 92, having substantially the same shape as the projected portion 94, at portions which contact the openings 11 of the tank 10. So, the space between the base plate 30 and the tank 10 can be closed for preventing volatilization of the solvent.

Example

The present invention is hereinafter to be described more specifically by the following examples. Such examples, however, are not to be construed as limiting in any way the scope of the present invention.

Example 1

The tank of the container was examined for volatile property using the container shown in FIG. 1. 20 ml of acetonitrile was poured in the container, and the base plate was placed on the tank. Then, the sheet according to the present invention was placed on the base plate, and then a lid made of polytetrafluoroethylene was set on the sheet. The container was left to stand in a refrigerator at 4° C., and every after 1 hour, 3 hours, 8 hours and 22 hours, the acetonitrile in the tank was weighed, and any reduced amount of the acetonitrile within a specified time was calculated for a volatile property test.

As the sheet, one having the radial slits (shown in FIG. 3(*c*)), the cut lines of which were conformed each other, was employed. As a sheet having elastic property, a sheet made of silicone rubber having a thickness of 0.5 mm was employed, and as a sheet having slip property, a sheet made of polytetrafluoroethylene having a thickness of 0.1 mm was employed (hereinafter, referring to as a conformed type sheet).

In addition, the sheets, made of the same material, were stacked by displacing the cut lines of the slits of the sheets at about 22.5° and employed for the same volatile property test (hereinafter, referring to as a displaced type).

Furthermore, the sheets, made of the same material and having no slit, were stacked and employed for the same volatile property test (hereinafter, referring to as a sealed type). Furthermore, the container, in which 20 ml of acetonitrile was poured, was left to stand in a refrigerator at 4° C. without the sheet placed thereon and employed for the same volatile property test (hereinafter, referring to as a no-lid type).

Figure 12:
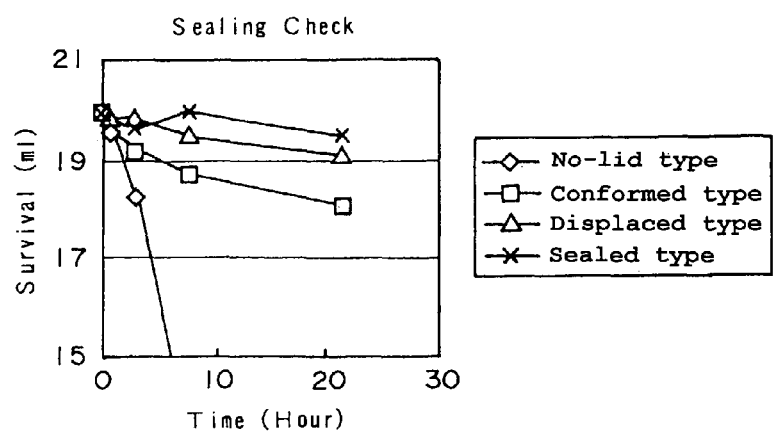
FIG. 12 A graph showing a result of the volatile property test.

Results are shown in Table 1. A numerical value in Table 1 means an amount (ml) of acetonitrile remaining in the tank. The results are also shown in FIG. 12. FIG. 12 is a graph showing a result of the volatile property test when the container is covered with each sheet. In the graph, the vertical axis means a time and the horizontal axis means a residual amount of acetonitrile in the container.

TABLE 1

|  | No-lid type | Conformed type | Displaced type | Sealed type |
| --- | --- | --- | --- | --- |
| 0 hour | 20.0 | 20.0 | 20.0 | 20.0 |
| 1 hour | 19.6 | 19.7 | 19.9 | 20.2 |
| 3 hours | 18.3 | 19.2 | 19.85 | 19.7 |
| 8 hours | 12.2 | 18.7 | 19.5 | 20.0 |
| 22 hours | 9.6 | 18.2 | 19.1 | 19.5 |

As shown in Table 1 and FIG. 12, in a case in which the container was left to stand at 4° C. without being covered with a lid, more than half amount of acetonitrile volatilized within 22 hours. And, in a case in which the container was sealed with the sheet, 19.5 ml of acetonitrile remained after 22 hours. In a case in which the container was sealed with the conformed type sheet according to the present invention, 18.2 ml of acetonitrile remained. And, in a case in which the container was sealed with the displaced type sheet according to the present invention, 19.1 ml of acetonitrile remained. These results show that the sheet according to the present invention can prevent volatilization of solvent in the container.

Example 2

In this example, the sheet was examined for durability to inserting and drawing of the tip. The test was carried out by using the container used in Example 1. And, the displaced type sheet in Example 1 was used. 10 ml of acetonitrile was poured in the tank, the tip was inserted through the slit into the tank and sucked 0.2 ml of acetonitrile, and then the sucked acetonitrile was placed back. Then, the tip was drawn out of the tank through the slit and reinserted through the slit. This procedure was repeated for 100 times at 20° C. The procedure period was 200 seconds. This series of procedure was repeated for 3 times. Then, acetonitrile remaining in the tank was weighed for obtaining a residual amount of acetonitrile. The result was shown in Table 2.

TABLE 2

|  | No-lid type (ml) | Displaced type (ml) |
|---|---|---|
| 1st | 9.7 | 10.0 |
| 2nd | 9.7 | 9.9 |
| 3rd | 9.6 | 10.0 |
| Average | 9.7 | 10.0 |

The displaced type sheet was examined by the naked eye whether or not the sheet was deformed. As the result, the sheet having slip property showed small deformation; however, the sheet having elastic property showed no deformation. So, it was found that conducting the inserting and drawing test about 100 times hardly deforms the composite sheet according to the present invention, whereby the test was smoothly carried out. As for volatilization of liquid, the container having no lid showed volatilization of a small amount of acetonitrile within 200 seconds; however, the container covered with the sheet according to the present invention shows little volatilization of acetonitrile. Accordingly, the sheet according to the present invention can maintain the container to be sealed even if the tip was inserted and drawn repeatedly.

Example 3

The tank of the container was examined for volatilization of water using the container shown in FIG. 7. 300 µl of water was poured to the container, and the base plate made of polytetrafluoroethylene was placed on the tank, further the sheet according to the present invention was placed thereon, and a lid made of stainless steel was placed thereon. The container was set in a constant-temperature bath of 37° C. and stirred at 400 $cm^{-1}$ rpm. After every 0.5 hour, one hour, 2 hours, 4 hours, 6 hours and 22 hours, the water remaining in the tank was weighed. And, an amount of water volatized within a specified period was calculated for the volatilization test.

The sheet having a radial slit, the cut lines of which were conformed each other (shown in FIG. 3(c)), was employed. As a sheet having elastic property, a sheet made of silicone rubber having a thickness of 0.5 mm was employed, and as a sheet having slip property, a sheet made of polytetrafluoroethylene having a thickness of 0.1 mm was employed (hereinafter, referring to as a conformed type sheet). Furthermore, the sheets made of the same materials and having no slit formed thereon was employed for the same test (hereinafter, referring to as a sealed type). Furthermore, the container having no sheet placed thereon was left to stand in a constant-temperature bath at 37° C. (hereinafter, referring to as a no-lid type).

Figure 13:
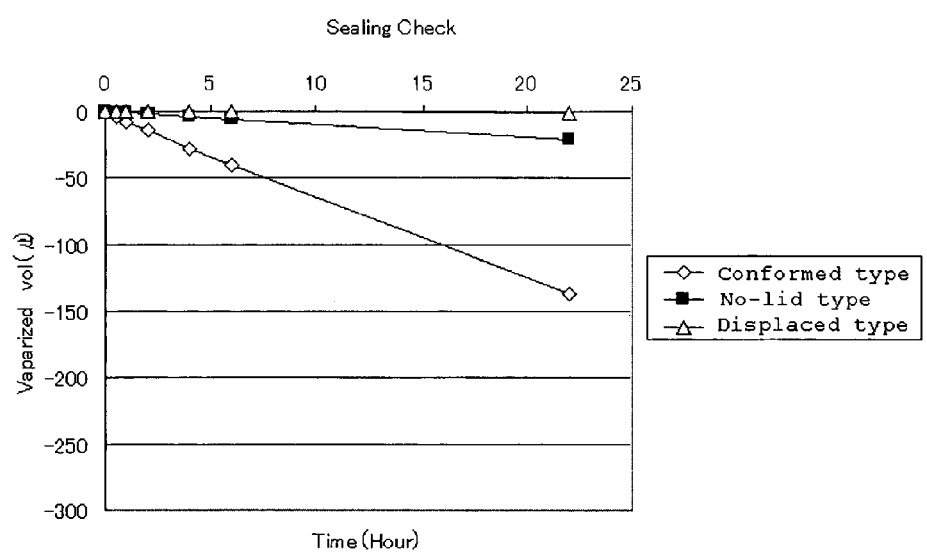
FIG. 13 A graph showing a result of the volatile property test.
Figure 14:
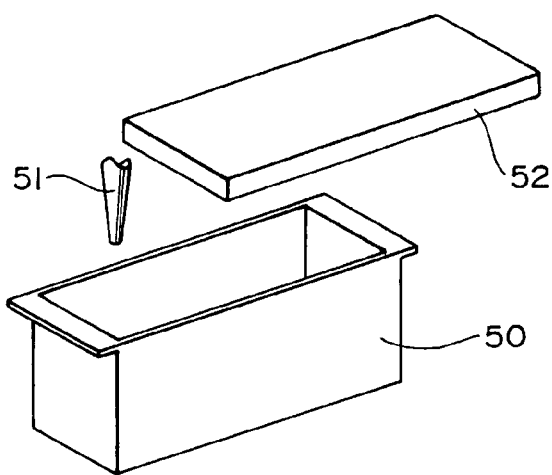
FIG. 14 A drawing showing conventional open type tank.
Figure 15:
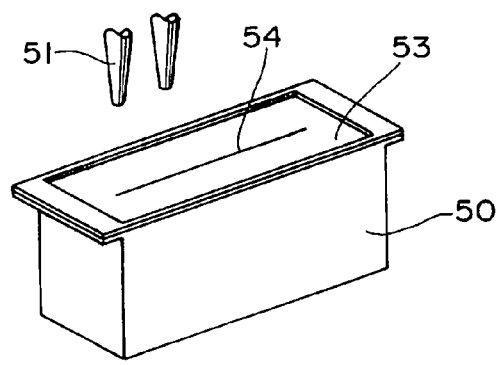
FIG. 15 A drawing showing conventional sealed type tand.
Figure 16:
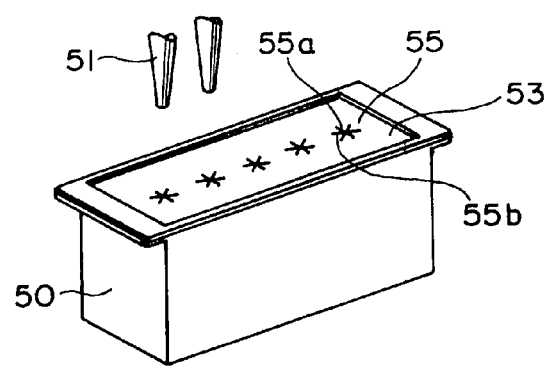
FIG. 16 A drawing showing another conventional sealed type tank.

Results were shown in Table 3. A numerical value shown in Table 3 means a ratio of an amount of the water remaining in the tank to the first amount of the water, which was represented by a capacity ratio. The results were also shown in FIG. 13. FIG. 13 is a graph showing the results of the volatilization tests of the containers each having a sheet placed thereon. In the graph, the vertical axis means a time and the horizontal axis means an amount of water remaining in the container.

TABLE 3

| Period | No-lid type | Displaced type | Sealed type |
|---|---|---|---|
| 0 | 100.0 | 100.0 | 100.0 |
| 0.5 | 98.6 | 99.8 | 100.0 |
| 1 | 97.3 | 99.6 | 100.0 |
| 2 | 95.3 | 99.3 | 100.0 |
| 4 | 90.7 | 98.7 | 99.9 |
| 6 | 86.4 | 98.1 | 99.9 |
| 22 | 54.3 | 93.0 | 99.9 |

As shown in Table 3 and FIG. 13, in a case in which the container was shaken under a condition of 37° C. without being covered with a lid, about half amount of the water volatilized within 22 hours. And, in a case in which the container was sealed with the sheet, most of the water remained after 22 hours. In a case in which the container was sealed with the sheet according to the present invention, 93% of the water remained. These results show that the sheet according to the present invention can prevent volatilization of solvent in the container.

What is claimed is:
1. A composite sheet comprising a sheet having elastic property and another sheet having slip property wherein said sheets are stacked vertically,
    wherein said sheet having elastic property and said sheet having slip property are both formed with a radial shaped slit, and
    said sheets are arranged such that centers of the radial shaped slits of said sheet having elastic property and said sheet having slip property are conformed to each other in the vertical direction and cut lines of said radial shaped slits of said sheet having elastic property and said sheet having slip property are not conformed to each other in the vertical direction.
2. The composite sheet according to claim 1, wherein said sheet having elastic property is made of silicone rubber.
3. The composite sheet according to claim 1, wherein said sheet having slip property is made of polypropylene, polyethylene or polytetrafluoroethylene.
4. The composite sheet according to claim 1, wherein said sheet having slip property has coefficient of dynamic friction and coefficient of static friction, the both of the coefficients being 0.2 or less.
5. The composite sheet according to claim 1,
    wherein said sheet having elastic property has hardness Hs of 30° to 90° and reflection coefficient of 20% to 50%.
6. The composite sheet according to claim 1, wherein a small insertion resistance is provided to a tip inserted into said radial shaped slits and said non-conformed cut lines of said radial shaped slits of said sheets provide a seal for said composite sheet.

7. A container for dispensing liquid contained therein through an opening,
   wherein said opening is closed with a composite sheet comprising a sheet having elastic property and another sheet having slip property wherein the sheets are stacked vertically,
   wherein said sheet having elastic property and said sheet having slip property are both formed with a radial shaped slit, and
   said sheets are arranged such that centers of the radial shaped slits of said sheet having elastic property and said sheet having slip property are conformed to each other in the vertical direction and cut lines of said radial shaped slits of said sheet having elastic property and said sheet having slip property are not conformed to each other in the vertical direction.

8. The composite sheet according to claim 7, wherein a small insertion resistance is provided to a tip inserted into said radial shaped slits and said non-conformed cut lines of said radial shaped slits of said sheets provide a seal for said composite sheet.

* * * * *

UNITED STATES PATENT AND TRADEMARK OFFICE
CERTIFICATE OF CORRECTION

PATENT NO. : 8,043,685 B2
APPLICATION NO. : 10/593747
DATED : October 25, 2011
INVENTOR(S) : Kiyoshi Yoshinari, Hideo Shimura and Kazumasa Kinoshita It is certified that error appears in the above-identified patent and that said Letters Patent is hereby corrected as shown below:

On the Title Page

Please correct the assignee information Item (73) as follows:

Delete: Chugai Seikaku Kabushikikaisha, Tokyo (JP)

And replace with: Chugai Seiyaku Kabushikikaisha, Tokyo (JP)
                                Biochromat Co., Ltd., Kanagawa (JP)

Signed and Sealed this
Fourteenth Day of August, 2012

David J. Kappos
*Director of the United States Patent and Trademark Office*